(12) United States Patent
Diaz

(10) Patent No.: US 6,695,850 B2
(45) Date of Patent: Feb. 24, 2004

(54) MINIMALLY INVASIVE TOTAL HIP REPLACEMENT

(76) Inventor: Robert L. Diaz, 123 Pembroke Dr., Palm Beach Gardens, FL (US) 33418

( * ) Notice: Subject to any disclaimer, the term of this patent is extended or adjusted under 35 U.S.C. 154(b) by 0 days.

(21) Appl. No.: 10/081,550

(22) Filed: Feb. 20, 2002

(65) Prior Publication Data

US 2003/0158559 A1 Aug. 21, 2003

(51) Int. Cl.[7] .............................................. A61B 17/58
(52) U.S. Cl. ....................................................... 606/91
(58) Field of Search ................................. 600/228, 235, 600/230; 128/882, 898; 606/90, 91, 86, 104; 602/32, 33, 34, 35, 39

(56) References Cited

U.S. PATENT DOCUMENTS 5,895,385 A * 4/1999 Guglielmi et al. ............ 606/32
6,010,535 A    1/2000 Mrugesh
6,315,718 B1  11/2001 Sharratt

* cited by examiner

*Primary Examiner*—Cary E. O'Connor
*Assistant Examiner*—Candice C. Melson
(74) *Attorney, Agent, or Firm*—McHale & Slavin, P.A.

(57) ABSTRACT

A surgical kit for minimally invasive total hip replacement includes a guide for inserting a guide wire into the body at the appropriate angle for reaming an Acetabulum. A shaft is inserted along the path of the guide wire. Working heads are sequentially attached to the shaft. The working heads of the reamers, impactors, trials and screw drivers are changed in the primary surgical incision thereby reducing the size of the incision and the trauma.

9 Claims, 2 Drawing Sheets

MINIMALLY INVASIVE TOTAL HIP REPLACEMENT

FIELD OF THE INVENTION

This invention relates to the field of orthopedic surgery and particularly to the instrumentation and methods for minimally invasive total hip replacement.

BACKGROUND OF THE INVENTION

A conventional total hip replacement is performed through a 10–14 inch incision located either anterior, lateral or posterio-lateral overlying the hip joint. The hip is dislocated either anteriorly or posteriorly.

This large incision is necessary to allow preparation of the acetabulum and proximal femur using instruments held at various angles to the acetabulum and proximal femur. The soft tissue dissection through skin, subcutaneous tissue, deep fascia, and muscles is associated with significant pain and time for healing.

The head and part of the neck of the femur is visualized and removed using a saw. The acetabulum is prepared by reaming to the desired size and using various sized trials until the optimum size is determined. The desired acetabular prosthesis is impacted in optimum position in the acetabulum and one of various sized liners is impacted into the posthesis. The prosthesis is fixed to bone either by cement or by porous coating that allows fixation by bony ingrowth into the prosthesis.

The proximal femur is then prepared by reaming and adjustment of neck length and varying sized trials are used to determine the optimum size. Trial neck lengths are used to determine the proper fit and leg length and the femoral stem is fixed top bone either by cement or porous coating on the prosthesis. The proper prosthetic head and neck length is then attached and the final fit, stability, and leg length are confirmed.

What is needed in the art is instrumentation along with procedures which reduce the soft tissue trauma and facilitate placement of the acetabular prosthesis.

DESCRIPTION OF THE PRIOR ART

U.S. Pat. No. 6,010,535 issued Jan. 4, 2000 to Shah discloses a surgical technique performed through arthroscopic and fluoroscopic guide procedures in which the natural ball of the Femur and the natural Acetabulum are left, largely, intact. A small hole is drilled through the Trochanter and ball of the Femur. The hole is extended, in the same plane, into the Acetabulum. A guide wire is inserted through the hole in the Femur and anchored in the Acetabulum. A reamer follows the guide wire enlarging the hole in the Femur to about an inch. Another reamer is inserted along the guide wire to ream a small spherical cavity in the natural Acetabulum. A small cup member is then secured in this cavity in the Acetabulum. A small ball may then attached to the exterior of the natural ball to be seated in the small cup member in the Acetabulum. The small ball and cup member, respectively, are secured by bone screws. This approach avoids the large conventional incisions with accompanying hospital stay and rehabilitation period. This procedure is obviously limited to those situations in which the ball-and-socket of the natural hip joint are still functional and pain free.

Sharratt, U.S. Pat. No. 6,315,718, issued Nov. 13, 2001, discloses the conventional surgical procedure for total hip replacement. Sharratt is concerned with the physical strength required on the part of the surgical team to retract and hold the Femur distant from the Acetabulum during surgery. To that end the patent is related to a surgical table mounted retractor apparatus capable of fixing the leg during surgery.

SUMMARY OF THE INVENTION

Accordingly, it is an objective of the instant invention to teach a minimally invasive technique for total hip replacement using a small incision to create a surgical field to visualize the acetabulum.

It is a further objective of the instant invention to teach the use of instrumentation to facilitate anatomically correct placement of an artificial acetabulum.

Another object of the invention is to teach the insertion of a properly oriented guide wire from the exterior of the patient's body into the surgical field.

It is yet another objective of the instant invention to teach the use of instrumentation with removable working heads for changing components within the surgical field.

The minimally invasive technique of this invention includes making a small, 2½ to 3 inches, incision to create a surgical field to view the head of the femur and the acetabulum during the preparation of each for implantation of the prosthesis. One end of a guide is inserted into the acetabulum through the surgical field and manipulated to the correct angle for reaming the acetabulum. This results in placing the other end of the guide at the proper point exteriorly of the patient's body to access the surgical field at the correct angle.

A guide wire is inserted through the other end of the guide and through the patient's body, at the correct angle, to engage the first end of the guide in the surgical field. In some cases, a second small incision, approximately 1 inch, is used for positioning the other end of the guide and inserting the guide wire. A common shaft may be inserted along the guide wire to operatively connect the surgical field and the exterior of the body, without an incision. As the stages of the hip replacement progress, the surgeon may replace different working heads on the end of the shaft which is in the surgical field without the necessity of removing the shaft from the body.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

The surgical approach for the minimally invasive hip replacement begins with an incision over the postero-lateral area of the hip approximately 3 to 5 cm. distal to the greater trochanter. The exact position of the incision depends upon the anatomical location of the trochanter in relation to the acetabulum. The incision extends approximately 2½ to 3 inches in a postero-superior direction, in line with the fibers of the Gluteus Maximus. The surgical field is increased exposing the posterior capsule of the hip.

The hip is dislocated by internal rotation providing lateral access and view of the acetabulum, along with the trochanter, neck of the Femur and ball. The exposed hip joint is evaluated to determine necessary repair. An osteotomy of the femoral neck may be performed and the head and neck of the femur removed and replaced with an artificial ball supported by a femoral rod, as part of the total hip replacement. Of course, other procedures may be indicated and performed.

Figure 1:
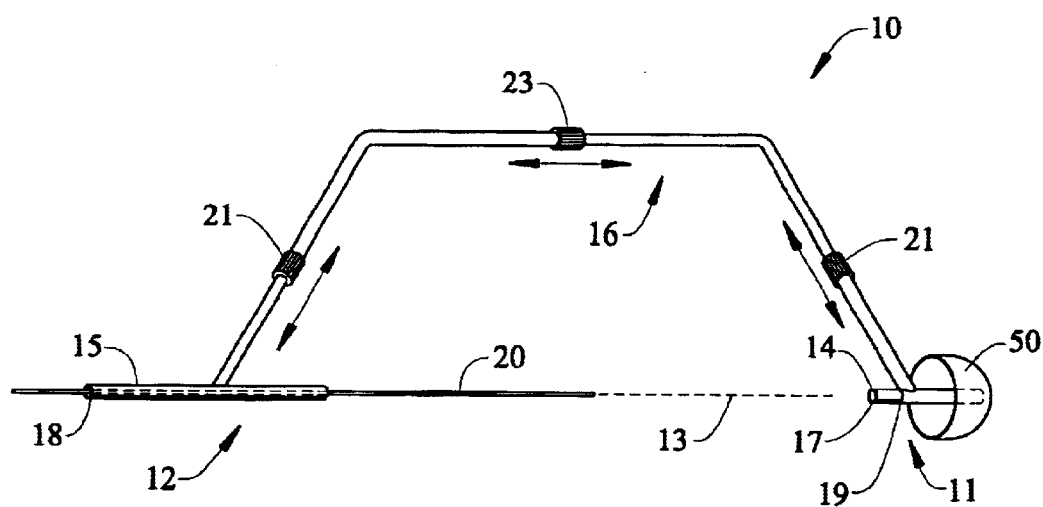
FIG. 1 is a side view of the acetabular alignment guide of this invention.

The acetabular alignment guide 10, shown in FIG. 1, is then used to determine the location of the insertion point of the guide wire. The leading end 11 is placed in the acetabulum. The leading end 11 has a dome shaped attachment 50 similar to the shape of the acetabulum and fits in the acetabulum. The leading end 11 is of a length to extend from the center of the acetabulum outwardly to a docking port 19 located within the surgical incision. The trailing end 12 of acetabular alignment guide 10 is then adjusted to obtain the desired angle used for preparation of the acetabulum by reaming, trialing, and, finally, impacting the acetabular prosthesis and liner. Depending on the size of the patient, the handle 16 attaching the leading end 11 and the trailing end 12 can be adjusted to accommodate the patient. As shown in FIG. 1, the height and length of the acetabular alignment guide is adjustable by couplings 21 and 23. The leading end 11 and the trailing end 12 of the guide 10 are separated by a space approximating the distance from the acetabulum and a point where an imaginary line from the acetabulum would exit the body and have a common longitudinal axis. In surgery, soft tissue occupies this space between the surgical field and the point on the skin where the imaginary line would exit. Both the leading end and the trailing end of the acetabular alignment guide have a bore or channel extending through the longitudinal axis 13. Leading end 11 has a channel 14 terminating in the docking port 19 and trailing end 12 has a through channel 15 in line with each other.

The handle portion 16, extending between the leading end and the trailing end, is strong and rigid enough to maintain the alignment of the channels 14 and 15. Further, the handle 16 may be used by the surgeon to secure the guide 10 once the final alignment is accomplished. The specific shape of the handle 16 is important only to the extent that it is displaced from the trailing end and leading ends to allow movement of the trailing end over the patient's body to orient the channels with the mouth of the acetabulum and locate the exit point. To this end the handle may be arched or angled. It may be integral with the leading and trailing ends or made of assembled parts. It may be made in different sizes and/or it may be adjustable in length.

The entire guide 10 may be made of materials acceptable for repeated surgeries or it may be disposable after a single use.

Once the acetabular alignment guide 10 has been manipulated to the proper position, the trailing end contacts the patient's skin in line with the optimum angle for reaming the patient's acetabulum. A small incision, e.g. one inch, may be made through the skin at the forward edge of the trailing end 12. A guide wire 20 or Steinman pin is inserted into the channel 15 through the small incision, through the intervening tissue and into channel 14 of the leading end. The resistance to farther insertion indicates the leading end of the guide wire 20 is in contact with the docking port 19 of the channel 14. This establishes the proper angle for reaming the acetabulum.

The channels 14 and 15 have an opening 17 and 18 along the bottom wall opposite the handle 16. Alternatively, the channels may be formed as bores with a removable lower wall portion, e.g. a telescoped lower wall to be removed after insertion of the guide wire or a laterally retractable partition. In any event, the guide wire 20 exits the guide 10 through the longitudinal openings 17 and 18 in the channels 14 and 15 as the handle is lifted from the patient's body leaving the guide wire in place.

Figure 2:
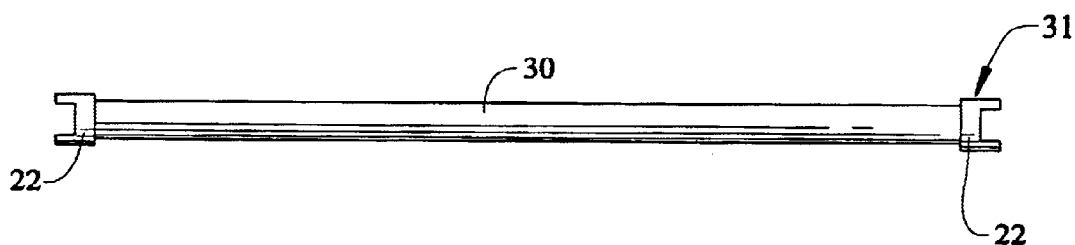
FIG. 2 is a side view of the instrument shaft changeable in the surgical field.

The common shaft 30, shown in FIG. 2, is inserted along the path of the guide wire between the surgical field and the exit point and small incision, if there is one. Once the shaft 30 is in place the guide wire 20 may or may not be removed, as desired by the surgeon. On the outside of the patient's body the shaft 30 may be connected to a power source or may be manually operated. The leading end 31 of the shaft appears in the surgical field. The surgeon fits a particular sized reamer, suitable to the patient's acetabulum size, to the shaft within the surgical field. The attachments 22 are conventional Hudson or Trinkle fittings.

Figure 3:
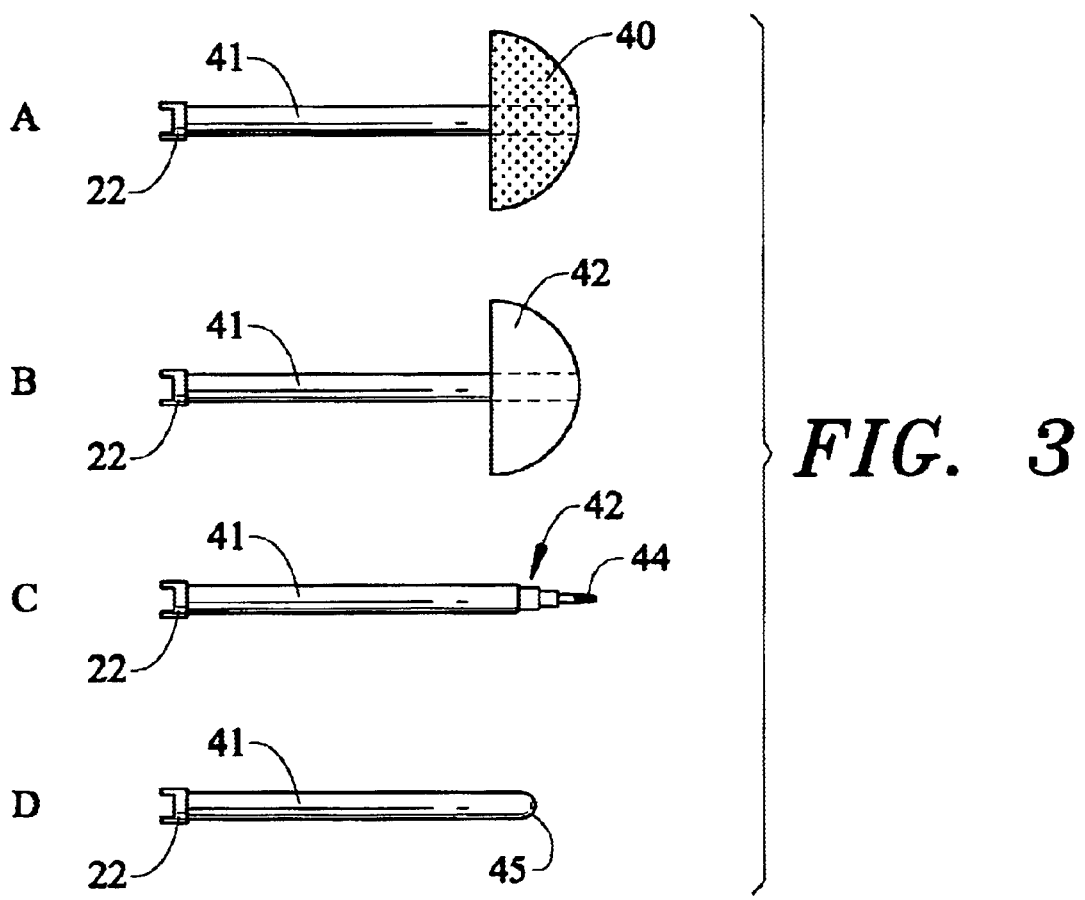
FIG. 3a is a side view of a working head reamer with a shaft connector.
FIG. 3b is a side view of a trial with a shaft connector.
FIG. 3c is a side view of a screw driver with a shaft connector.
FIG. 3d is a side view of an impactor with a shaft connector.

As shown in FIG. 3, the reamer or other working head, may be provided with a short shaft 41 for ease of connection with the elongated shaft 30. Alternatively, each working head could be supplied with its own shaft or the shaft 30 could be connected directly to the working head.

As the acetabulum is progressively cleaned, larger reamers may be exchanged through the surgical field, without changing shafts, until the a suitable size is obtained.

At this point, a trial artificial acetabulum 42 is placed on the end of the shaft 30, in the incision, for ascertaining the best union with the pelvic bone. Several different trials 42 may be needed before an acceptable fit. Once selected, the properly sized artificial acetabulum is then driven into place by the impactor 45 attached to the shaft 30. The acetabulum liner is then inserted and attached.

The artificial acetabulum may require bone screws for additional support. In that case, the shaft 30 is attached to a screw driver 44 inserted to tighten the screws. The screw driver shaft 41 may be fitted with a hinge 43 to accommodate different screw angles.

Once the acetabulum is securely in place, the guide wire is withdrawn through the minor incision and it is closed. The remaining procedures of the total hip replacement may be accomplished in the major surgical field. Upon completion, it is closed.

This procedure obviates the need for lengthy incision to properly position an instrument to ream, trial, and impact an acetabular prosthesis and liner. This invention improves subsequent hospital care and patient rehabilitation.

The instruments of this invention may be supplied individually or as a kit.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A wire guide for use in orthopedic surgery to reduce surgical trauma comprising an elongated generally U-shaped handle having a first free end and a second free end connected by an intermediate portion, said first free end connected to a leading end of a wire guide, said second free end connected to a trailing end of said wire guide, said leading end and said trailing end separated by an empty space approximate in length to said intermediate portion of said handle, said leading end having a first channel, said trailing end having a second channel, said first channel and said second channel separated by said empty space, said first channel and said second channel each having a common longitudinal axis, said first channel and said second channel adapted to receive a guide wire and direct it along said common longitudinal axis.

2. A guide of claim 1 wherein said first channel in said leading end and said second channel in said trailing end each have an open portion adapted for removal from the guide wire.

3. A guide of claim 1 wherein said intermediate portion is parallel with said longitudinal axis.

4. A guide of claim 1 wherein said elongated handle is adjustable.

5. A guide of claim 1 wherein said first channel in said leading end terminates in a docking port, said docking port adjacent said trailing end.

6. A guide of claim 5 wherein said first channel in said leading end and said second channel in said trailing end each have an open portion adapted for removal from said guide wire.

7. A method of minimally invasive hip replacement of a patient comprising the steps of (a) providing a guide having a leading end spaced apart from a trailing end, said leading end and said trailing end having a common longitudinal axis, said leading end and said trailing end having a channel along said common longitudinal axis, said leading end and said trailing end connected by a laterally displaced handle;

(b) placing said leading end in contact within a surgical field with an exposed acetabulum of the patient;

(c) manipulating said handle to ascertain the center of said acetabulum;

(d) placing said trailing end in contact with the patient;

(e) inserting a guide wire through said channel in said trailing end into said channel in said leading end of said guide; and (f) removing said guide from said guide wire.

8. A method of claim 7 including the steps of (a) inserting an elongated shaft along said guide wire into said surgical field;

(b) connecting one end of said shaft to a working head in said surgical field;

(c) connecting said other end of said shaft to a power source;

(d) applying power to said working head in said surgical field; and (e) changing working heads in said surgical field as required.

9. A surgical kit for minimally invasive total hip replacement said kit comprising a guide having an elongated handle connected at one end to a leading end and connected at the other end to a trailing end, said leading end and said trailing end having a channel, a guide wire adapted to be received in said channel, at least one shaft having a connector on one end for attachment to a source of power and a connector on the other end for attachment to working heads, said working heads including a plurality of different sized reamers for the acetabulum, said reamers each having a connector for said shaft, a plurality of different sized trials for said acetabulum, said trials having a connector for said shaft, an impactor tool for impacting the acetabulum, said impactor tool having a connector for said shaft, and a screw driver for inserting bone screws, said screw driver having a connector for said shaft.

* * * * *